United States Patent [19]

Yamada et al.

[11] Patent Number: 5,342,766
[45] Date of Patent: * Aug. 30, 1994

[54] **PROCESS FOR PRODUCING L-THREONINE BY FERMENTATION WITH *P. RETTGERI*.**

[75] Inventors: Katsushige Yamada; Kyousuke Yotsumoto, both of Aichi, Japan

[73] Assignee: Toray Industries, Inc., Japan

[*] Notice: The portion of the term of this patent subsequent to Mar. 24, 2009 has been disclaimed.

[21] Appl. No.: 3,840

[22] Filed: Jan. 11, 1993

Related U.S. Application Data

[63] Continuation of Ser. No. 660,909, filed as PCT/JP85/00468, Feb. 27, 1991, abandoned, which is a continuation of Ser. No. 913,668, Sep. 3, 1986, abandoned.

[51] Int. Cl.$^5$ .......................... C12P 13/08; C12N 1/20
[52] U.S. Cl. ................... 435/115; 435/172.1; 435/873; 435/252.1
[58] Field of Search ................. 435/115, 172.1, 173.8, 435/873, 252.1

[56] References Cited

U.S. PATENT DOCUMENTS 3,375,173  3/1968  Nishimura et al. ............... 435/115
3,893,888  7/1975  Tsuchida et al. ................ 435/115

OTHER PUBLICATIONS

Ikeda et al., *Agr. Biol. Chem* 40, pp. 511–516, 1976.
Yoshinaga et al. In "Amino Acids, Biosynthesis and Genetic Regulation", 1983, Addison Wesley, pp. 405–428.
Stanbury et al, "Principles of Fermentation Technology", 1984, pp. 41–47, Pergamon Press.

*Primary Examiner*—Irene Marx
*Attorney, Agent, or Firm*—Austin R. Miller

[57] ABSTRACT

Higher amount of L-threonine can be accumulated by the cultivation of certain microorganism belonging to the genus Providencia, having a resistance to methionine antagonist and having capabilities of producing L-threonine.

2 Claims, No Drawings

PROCESS FOR PRODUCING L-THREONINE BY FERMENTATION WITH P. RETTGERI.

This application is a continuation of application Ser. No. 07/660,909 filed as PCT/JP85/00468, Feb. 27, 1991, now abandoned which is a continuation of application Ser. No. 06/913,668 filed Sep. 3, 1986, now abandoned.

FIELD OF ART

This invention relates to a process for producing L-threonine by fermentation.

BACKGROUND ART

Hitherto, the methods using L-isoleucine requiring mutant (Japanese Examined Patent Publication No. 4440/1968) or using the mutant having a resistance to α-amino-β-hydroxyvaleric acid and requiring L-isoleucine (Abs.) Ann. Meet. Agric. Chem. Sec. Japan, p 9, (1970)) have been known with respect to production of L-threonine by fermentation with using certain microorganisms of the genus Providencia (The species *rettgeri* was classified as genus Proteus before.)

However, there is room for further improvement in the capability of the strains as to the accumulation of L-threonine in the method using the above-mentioned microorganisms.

DISCLOSURE OF THE INVENTION

As a result of the present inventors' earnest investigation for more profitable production of L-threonine by fermentation process, the inventors have found that certain mutants of genus Providencia which are resistant to methionine antagonist, accumulate a large amount of L-threonine.

Thus, the present invention is a process for producing L-threonine by fermentation comprising
(a) cultivating an L-threonine-producing microorganism belonging to the genus Providencia until L-threonine is accumulated in a culture medium, said microorganism having a resistance to methionine antagonist and
(b) recovering the L-threonine from the culture broth.

The methionine antagonist-resistant mutant of the genus Providencia has not yet been isolated. Moreover, it has not been previously known that a large amount of L-threonine can be secreted and accumulated in the culture broth by the methionine antagonist-resistant mutant belonging to the genus Providencia.

THE BEST FORMS TO PRACTICE THE INVENTION

The present invention will be described in further detail hereinafter.

The microorganisms used in the invention belong to the genus Providencia (the genus is decided according to Bergy's Manual of Systematic Bacteriology, 9th edition, pages 494 to 496) and have a resistance to methionine antagonist. In the invention, preferable examples of the methionine antagonists are ethionine, norleucine. crotonylalanine, crotonylglycine, methionine sulfoxime, and so on. The microoragisms used in the present invention include the strains which have at least the above-mentioned character, even though these strains have other requirements for growth thereof or a resistance to other chemical compounds.

The preferable microorganisms employed in the invention require L-isoleucine and have a resistance to feedback control by L-threonine in addition to the above-mentioned resistance.

That is, in the invention there can be used methionine antagonist-resistant mutants which acquire the effective character for L-threonine secretion. For example, a mutant requiring L-isoleucine, having a resistance to α-amino-β-hydroxyvaleric acid through the conventional artificial mutation may be used.

In the present invention, mutants requiring L-isoleucine for the growth thereof means wide concept and includes leaky type, namely incomplete defect type, and further includes the case when the growth requirement is satisfied with biosynthetic precursors of L-isoleucine, The specimens of the microorganisms used in The present invention are as follows:
(a) *Providencia rettgeri* TY-1 (FERM BP-871)
(b) *Providencia rettgeri* TY-2 (FERM BP-872).

These mutants have a resistance to L-ethionine among methione analogs and were derived from *Providencia rettgeri* IN4-7H (having a resistance to α-amino-β-hydroxyvaleric acid, requiring L-isoleucine). *Providencia rettgeri* IN4-7H was derived from *Providencia rettgeri* ATCC 21118 (requiring L-isoleucine), These mutants can be relatively easily obtained by conventional mutation methods. Namely, in the case of obtaining the methionine antagonist-resistant mutant, the parental cells are irradiated with ultraviolet light or treated with mutagene (for example, N-methyl-N'-nitro-N-nitrosoguanidine or ethylmethane sulfonate), and said resistant mutant is obtained on the agar plate containing so high concentration of methionine antagonist to prevent the parental strain from growing.

The strain having a resistance to methionine antagonists in the present invention is defined as a strain of which growth degree in the culture medium supplemented with 4 mg/ml of methionine antagonist is at least 50%, preferably at least 70%, based on the case in the absence of methionine antagonist. In the invention, growth degree is shown by the relative optical density of culture broth at 660 nm when the optical density of culture broth in non-supplement of methionine antagonist is defined as 100%. Methionine antagonists such as ethionine, used to examine resistance can be commercially available materials.

In the present invention, L-threonine producing culture medium is a conventional medium containing carbon source, nitrogen source, inorganic ions, and if necessary, other organic minor ingredients.

The preferable culture medium may contain 2 to 15% of carbon sources; Examples include:
carbohydrates such as glucose, fructose, hydrolysate of starch or cellulose, or molasses;
organic acids such as fumalic acid, citric acid, or succinic acid;
alcohols such as glyceral and contain 0.5 to 4.0% of nitrogen source, including for example, organic ammonium salts such as ammonium acetate;
inorganic ammonium salts such as ammonium sulfate, ammonium chloride, ammonium phosphate, or ammonium nitrate;
ammonia gas;
aqueous ammonia;
urea.

The medium also may contain 0.001 to 0.4% of required materials such as L-isoleucine, and if necessary, may contain 0 to 4% or corn steep liquor, polypeptone, or yeast extract and the like as an organic minor nutrient. In addition, small amount of potassium phosphate, magnesium sulfate, ferrous sulfate 7-hydrate, 4- to 6-hydrate of manganese sulfate, etc. may be added to the culture medium.

Cultivation is carried out preferably under aerobic conditions. A preferable result is obtained by adjusting the pH of the medium from 5 to 9, controlling the temperature from 24° to 37° C. during cultivation, and shaking or stirring with aeration for 48 to 120 hours.

An optional process for cultivation includes, for example, any of continuous operation, semi-continuous operation and batch operation.

The recovery or L-threonine from the culture broth is carried out, for example, by the following method.

The culture broth from which the cells are removed is adjusted to pH 2 with hydrochloric acid. Then the broth solution is passed through the strongly acidic ion exchange resin, and the adsorbant is eluted by dilute aqueous ammonia. Ammonia is evaporated and then the resulting solution is condensed. Alcohol is added to the concentrate, and then, crystals formed under cooling are collected, and then L-threonine can be obtained.

EXAMPLE 1

A. (Isolation of the mutant strains having a resistance to L-ethionine.)

The cells of *Providencia rettgeri* IN4-7H (which has a resistance to α-amino-β-hydroxyvaleric acid and requires L-isoleucine for growth) were irradiated with ultraviolet light by a conventional method. These cells were spread on the agar plate (which contained glucose 1.0%, ammonium sulfate 0.3%, potassium monohydrogen phosphate 0.05%, potassium dihydrogen phosphate 0.15%, magnesium sulfate 7-hydrate 0.04%, L-isoleucine 0.01%) supplied with 10 g/l L-ethionine. Then, after incubation for 4 to 6 days at 30° C., large colonies formed on the plate were picked up, and L-ethionine-resistant strains (*Providencia rettgeri* TY-1 and TY-2) were obtained.

B. (Degree of resistance of L-ethionine-resistant mutants)

Each strain shown in Table 1 was cultivated in bouillon liquid medium at 30° C. for 16 hours with shaking, and the grown cells were harvested and washed with physiological saline.

The resulting cell suspension was inoculated into 5 ml of the minimal medium (composition: glucose 1.0%, ammonium sulfate 0.3%, potassium monohydrogen phosphate 0.05%, potassium dihydrogen phosphate 0.15%, magnesium sulfate 7-hydrate 0.01%, L-isoleucine 0.01%) containing 0 g/l, 4 g/l, 8 g/l, 16 g/l of L-ethionine, respectively, and cultivated at 30° C. for 24 hours. The growth degree or each strain was measured.

The results are shown in Table 1, and the growth of L-ethionine-resistant mutants (*Providencia rettgeri* TY-1 and TY-2) used in the present invention are not inhibited in the presence of the high concentration of L-ethionine. These mutants, therefore, have a strong resistance to L-ethionine.

TABLE 1

| Strains | Relative growth degree*) (%) Amount of L-ethionine added (g/l) | | | |
| --- | --- | --- | --- | --- |
| | 0 | 4 | 8 | 16 |
| Parent strain *Providencia* | 100 | 18 | 2 | 0 |

TABLE 1-continued

| Strains | Relative growth degree*) (%) Amount of L-ethionine added (g/l) | | | |
| --- | --- | --- | --- | --- |
| | 0 | 4 | 8 | 16 |
| *rettgeri* IN4-7H | | | | |
| This invention strains | | | | |
| *Providencia rettgeri* TY-1 | 100 | 79 | 77 | 71 |
| *Providencia rettgeri* TY-2 | 100 | 84 | 97 | 80 |

*)Relative growth degree is shown by the relative optical density of the culture broth at 660 nm when the optical density of the culture broth in the absence of L-ethionine is 100%.

EXAMPLE 2

The 50 ml of fermentation medium, which had the following composition, in 1-liter erlenmeyer flask was sterilized at 120° C. for 10 minutes.

The 5 ml of culture broth of each strain shown in Table 2, which was cultivated at 30° C. for 16 hours with shaking in a seed culture medium containing 2% of glucose, 1% of polypeptone, 1% of yeast extract and 0.5% of NaCl, was put into the fermentation medium and then was cultivated at 30° C. for 90 hours with shaking condition of 150 rpm and 3 cm-stroke.

| Fermentation medium composition | |
| --- | --- |
| Glucose | 8% |
| $(NH_4)_2SO_2$ | 2% |
| $KH_2PO_4$ | 0.1% |
| $MgSO_4 \cdot 7H_2O$ | 0.04% |
| $Fe^{++}$ | 2 ppm |
| $Mn^{++}$ | 2 ppm |
| L-isoleucine | 0.005% |
| $CaCO_3$ (sterilized separately) | 3% |
| pH (neutralized with KOH) | 7.0 |

TABLE 2

| | Strain | Amount of L-threonine accumulated (g/l) |
| --- | --- | --- |
| Comparative Example | *Providencia rettgeri* IN4-7H | 6.0 |
| This invention Examples | *Providencia rettgeri* TY-1 | 10.6 |
| | *Providencia rettgeri* TY-2 | 10.4 |

After cultivation, the amount of L-threonine in the flitrate which was obtained by removing the cells and calcium carbonate from the culture broth was quantitatively analyzed by automatic amino acid analyzer (produced by ,Japan Electric Co. JLC-200A), and the results shown in Table 2 were obtained.

EXAMPLE 3

Each strain shown in Table 3 was cultivated in bouillon liquid medium at 30° C. for 16 hours with shaking, and this culture broth was inoculated by 10% by volume into a small glass jar fermentor containing 800 ml of the same fermentation medium as used in Example 2 except that 0.5% of $(NH_4)_2SO_4$ and 4.0% of glucose were used. Cultivation with aeration (1 vvm) and agitation (800 rpm) was started at 30° C.

Control of the pH and feed of the nitrogen source were served with 25% aqueous ammonia and the pH was kept between 6.5 to 8.0. Cultivation was carried out with intermittent feeding of glucose, $KH_2PO_4$ and $MgSO_4 \cdot 7H_2O$ for 70 hours and the results shown in Table 3 were obtained.

TABLE 3

| | Strain | Amount of L-threonine accumulated (g/l) |
| --- | --- | --- |
| Comparative Example | *Providencia rettgeri* IN4-7H | 8.1 |
| This invention Example | *Providencia rettgeri* TY-1 | 19.0 |

The cells were removed from the culture broth of *Providencia rettgeri* TY-1. 500 ml of the resulting flitrate was passed through the column packed with strong cation exchange resin DIAION (Trade Name) SK.1B (H type). Then, the column was washed with water and thereafter the adsorbant in the column was eluted by 2 N aqueous ammonia. The eluent was concentrated under reduced pressure after decoloriging. Ethanol was added to the resultant and left standing under cooling, and then the crystals formed were collected, dried to give 8.4 g of L-threonine having over 96% of purity.

INDUSTRIAL APPLICABILITY OF THE INVENTION

L-threonine is one or the essential amino acids and known to be important as medicine and feed additive.

We claim:

1. A process for producing L-threonine by fermentation comprising
   (a) culturing *Providencia rettgeri* FERM BP-871(TY-1) in an aqueous nutrient medium containing assimilable sources of carbon, nitrogen and inorganic substances and
   (b) recovering the L-threonine from the culture broth.

2. A process for producing L-threonine by fermentation comprising
   (a) culturing *Providencia rettgeri* FERM BP-872(TY-2) in an aqueous nutrient medium containing assimilable sources of carbon, nitrogen and inorganic substances and
   (b) recovering the L-threonine from the culture broth.

* * * * *